United States Patent [19]

Ackland et al.

[11] Patent Number: 4,789,635
[45] Date of Patent: Dec. 6, 1988

[54] APPARATUS FOR DETECTING MICRO-ORGANISMS

[75] Inventors: Martin R. Ackland; Roderick M. De'Ath, both of Wantage, England

[73] Assignee: Metal Box p.l.c., United Kingdom

[21] Appl. No.: 4,895

[22] Filed: Jan. 20, 1987

[30] Foreign Application Priority Data

Feb. 6, 1986 [GB] United Kingdom ............... 8602980

[51] Int. Cl.⁴ .................................................. C12M 1/36
[52] U.S. Cl. ..................... 435/291; 435/300; 435/809; 422/102; 73/864.91
[58] Field of Search .......... 73/864.91, 864.82, 864.85; 356/246; 422/102, 104; 436/150; 435/34, 173, 291, 299–301, 809

[56] References Cited

U.S. PATENT DOCUMENTS

| | | | |
|---|---|---|---|
| 3,526,125 | 9/1970 | Gilford et al. | 73/864.91 X |
| 3,680,967 | 8/1972 | Engelhardt | 356/246 |
| 4,096,965 | 6/1978 | Lessnig et al. | 220/20 |
| 4,290,550 | 9/1981 | Chulay et al. | 233/26 |
| 4,310,488 | 1/1982 | Rahm et al. | 422/102 |
| 4,517,851 | 5/1985 | Tice | 73/864.91 |
| 4,653,337 | 3/1987 | Ackland et al. | 73/866.5 |

FOREIGN PATENT DOCUMENTS

WO85/00225  1/1985  PCT Int'l Appl.
2142433  1/1985  United Kingdom.
2171982  9/1986  United Kingdom.

Primary Examiner—Samuel Scott
Assistant Examiner—Allen J. Flanigan
Attorney, Agent, or Firm—Diller, Ramik & Wight

[57] ABSTRACT

Apparatus for detecting micro-organisms comprises a rack having an array of stations at which a plurality of microbiological sample containers can be received. Each container is provided with an electrode or electrodes at its base for connection with electrical contacts on the base of the rack, and container retention means in the form of a cap with a bayonet joint or screw-threaded connection for releasably retaining the containers in the rack are adapted to be operable from above the upper support plate of the rack.

12 Claims, 3 Drawing Sheets

000
APPARATUS FOR DETECTING MICRO-ORGANISMS

BACKGROUND OF THE INVENTION

1. Field of the Invention

The present invention relates to apparatus for use in detecting micro-organisms in samples of a substance and can be used, for example, for monitoring substances intended for human consumption, such as foods, drinks or pharmaceuticals, or may be used to monitor pathological samples, such as blood, in the laboratory.

2. Description of the Prior Art

Blood culturing techniques currently used in hospitals include a method in which a sample of blood is cultured in nutrient broth, from which samples are subcultured on agar plates at regular intervals. Not only is this method extremely slow with results not being expected for several days, but it is highly labour intensive and requires good aseptic conditions to be maintained throughout.

A quicker technique uses a machine sold under the trade name Bactec. To use this machine, the sample is exposed to a radioactive substrate which is consumed by the micro-organisms, which then give off radioactive carbon dioxide for detection by the machine. Although this machine gives results in hours, rather than days, hospital personnel may be worried by possible radioactive exposure and waste disposal.

Electrochemical methods have been proposed which include measuring conductance, impedance or potential difference changes, but known apparatus using these methods is not readily susceptible to hospital use in that the sample bottles are kept at a controlled temperature in a water bath which may become contaminated by spillage. In another known apparatus, instead of sample-holding bottles, special modules are required which are not suitable for filling directly from the hypodermic syringe used to remove blood from a patient, and an intermediate pipetting stage is necessary, with the result that time is wasted, labour is required and spillage, and hence contamination of personnel or equipment, is possible.

In our British Patent Specification No. 2,142,433B, we have described apparatus for use in detecting micro-organisms in any one of a plurality of samples, comprising a plurality of containers for the samples, each container having in its base at least one electrode contactable with the sample therein, and a container-mounting member having means for receiving and for locating each of said containers at a respective one of an array of stations, the container-mounting member comprising a base provided with electrical contact means at each station for electrical connection with the electrode of a container received at that station.

SUMMARY OF THE INVENTION

It is an object of the present invention to provide apparatus for detecting micro-organisms which is suitably robust and convenient to use and which is easy to keep clean in a hospital environment.

According to the present invention there is provided apparatus for use in detecting micro-organisms in any one of a plurality of samples, comprising a plurality of containers for the samples, each container having in its base at least one electrode contactable with the sample therein; a container-mounting rack having means for receiving and for locating each of said containers at a respective one of an array of stations, the container-mounting rack having a base and upper support means spaced upwardly from said base, electrical contact means being provided on the base at each said station for electrical connection with the electrode of a container received at the respective station; and releasable retention means, for retaining a container at a station, which are adapted to co-operate with the upper support means of the container-mounting rack and are operable from above said upper support means.

As a result of placing the electrodes in the base of the sample containers, there are no wires protruding from the containers which may become contaminated or tangled. Moreover, because the retention means are operable from above the upper support means of the container-mounting rack, access to each container is good with the result that the containers are readily inserted and removed from their stations in the rack.

Suitably, the location means for locating a said container at one of said stations is disposed adjacent the respective electrical contact means at that station. As a result, there is good positive location of a container in the rack where it is most needed to ensure that good electrical contact between the containers and the rack is established.

The retention means may comprise either means for screw-threaded engagement or bayonet engagement means between each container and the upper support means.

The location means suitably comprises a push-fit plug and socket means, which is preferably rotationally independent of the retention means.

Suitably, where each container has more than one electrode in its base, with a respective number of electrical contacts being provided at each station, the apparatus may further comprise orientation means for orienting the container at the respective station so that the electrodes make electrical connection only with their respective electrical contacts.

In the case where the location means comprises a push-fit plug and socket means, the orientation means may comprise a mutually engageable key and keyway on the plug and socket means. Since the retention means is rotationally independent of the push-fit plug and socket means, the container may be retained at a station in the rack without rotational interference presented by the engagement between the key and keyway on the plug and socket means.

Suitably, the container-mounting rack comprises heating means for incubating samples in containers which are received in the rack.

The container-mounting rack may further comprise a containment vessel at each station adapted to surround a container received at that station and contain spillage therefrom. Suitably, each said vessel is adapted to be releasably attached to the container-mounting rack.

The upper support means of the rack may comprise substantially a horizontal plate provided with an indented region at each station for retaining spillage from a container at or adjacent that station.

DETAILED DESCRIPTION OF THE INVENTION

Figure 1:
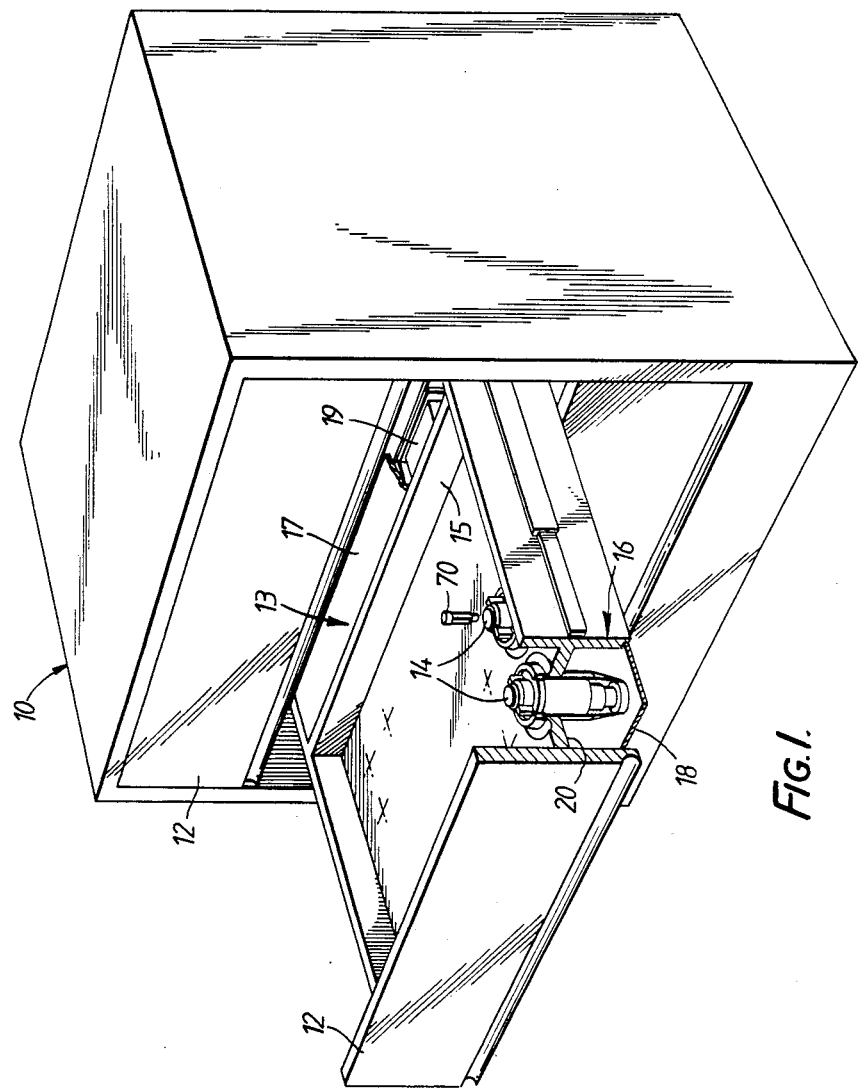
FIG. 1 is a perspective view of a three drawer cabinet, each drawer housing apparatus according to the invention.

Referring to FIG. 1 of the drawings, there is shown a cabinet 10 having three drawers 12, each of which houses apparatus according to the invention. The apparatus generally comprises a plurality of containers 14 which are releasably received at a respective station in a container-mounting rack 16, housed one in each drawer 12. At the back of each drawer 12 is a compartment 13 separated from the rack 16 by a wall 15 and closed at the top by a removable cover plate 17; the purpose of this compartment will be described hereinbelow.

The rack 16 is generally frame-like and comprises a base 18 and a support plate 20 arranged substantially parallel thereto and spaced therefrom. The upper support plate 20 is provided with an array of apertures 22 (FIG. 2) through which the containers 14 are insertable. The support plate 20 acts to support the containers in an upright position.

Figure 2:
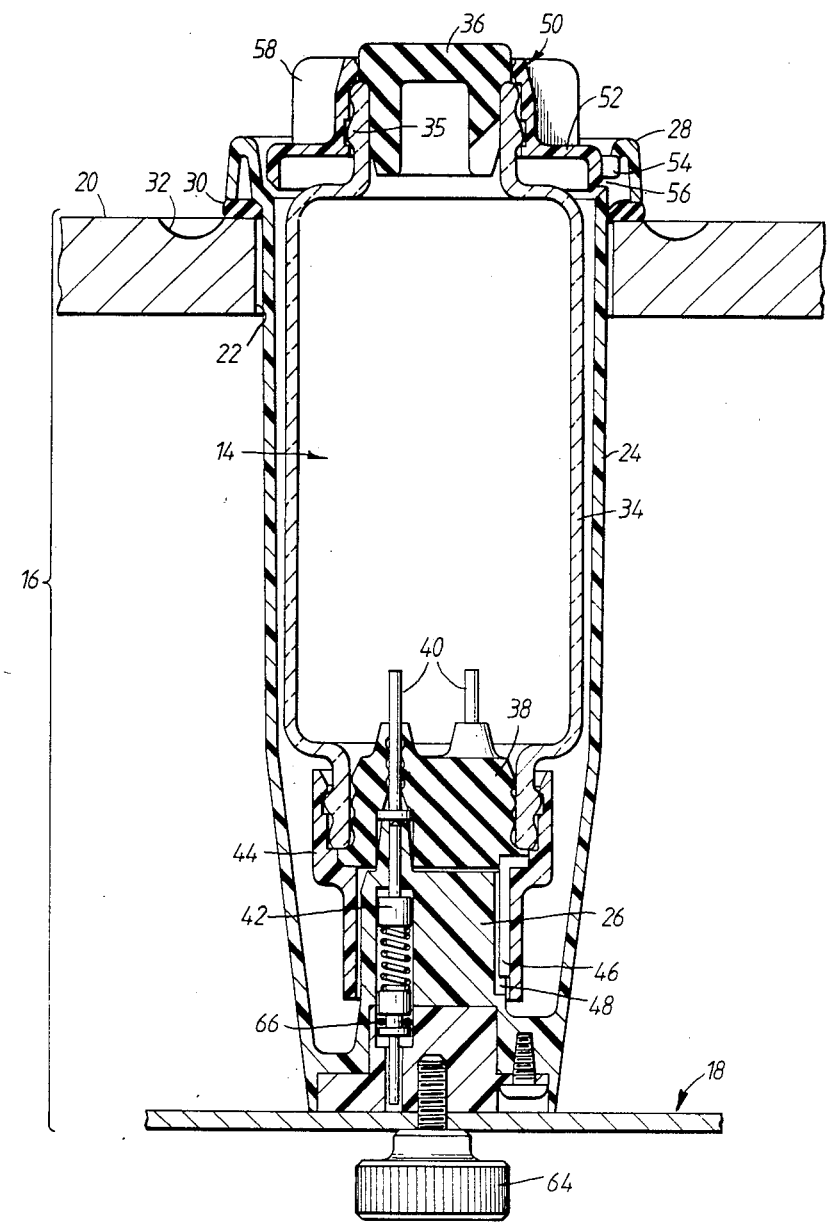
FIG. 2 is an enlarged longitudinal cross-section through one of the sample containers retained at a station in the rack shown in FIG. 1.

FIG. 2 shows in greater detail a sample container 14 received and located at a station in the container-mounting rack 16. Extending between the base 18 and upper support plate 20 at each station is a bucket-shaped containment vessel 24 integrally formed at its base with a spigot 26, which acts as location means for the container 14 and which will be described in greater detail below. The upper edge of the containment vessel 24 is turned back on itself to form a collar 28 which hooks over the rim of the aperture 22 in the upper support plate 20. The containment vessel 24 serves to catch any inadvertent spillage from the container 14 thus preventing spread of contaminating substances to the rest of the apparatus. A seal 30 ensures that no spillage on the upper surface of the plate 20 leaks down into the space between the aperture 22 in the wall and the outer wall of the containment vessel 24. An indented circular channel 32 in the support plate 20 and surrounding the collar 28 of the containment vessel 24 helps to catch spills and stop them spreading over the upper surface of the plate 20.

The container 14 consists of a substantially cylindrical glass body 34 sealed at both ends by elastomeric bungs 36,38. The lower bung 38 houses a pair of electrodes 40 which make electrical connection with a respective pair of electrical contacts 42 housed in the spigot 26 of the rack 16. By means of a crown fitting, a generally cylindrical socket member 44 is secured to the lower neck of the container body 34 and holds the bung 38 captive in the neck of the container body 34. The socket member 44 is adapted to be received on and located by the spigot 26. A detailed description of the construction of the container 14 and its location on the spigot 26 with resultant electrical connection between the electrodes 40 of the container 14 and the electrical contacts 42 of the spigot 26 is given in our British patent application No. 8,506,097, published under No. 2,171,982.

To ensure correct orientation of the electrodes 40 with their respective electrical contacts 42, there is provided a key in the form of an axially extending rib 46 on the inner surface of the socket member 44 and this is engageable with a keyway 48 on the spigot 26.

To ensure that a container 14 is retained within the rack 16, thus maintaining good and reliable electrical contact between the electrodes 40 and contacts 42, the apparatus comprises retention means, which consist in the case of the embodiment illustrated in FIGS. 1 and 2 of a bayonet joint means. Secured to the upper neck 35 of the container body 34 is a cap 50 having an outwardly extending skirt portion 52, from which projects at least one lug 54 engageable with a slot opening 56 in the collar 28 of the containment vessel 24. Projecting either side of the cap 50 is a pair of wings 58 which enable the cap 50 to be turned when engaging or disengaging the bayonet joint means 54,56.

To allow the retention means to operate, whilst enabling the push-fit socket member 44 to be urged vertically downwards on to the spigot 26 once the key and keyway 46,48 are in operation, the cap 50 is secured to the upper neck 35 of the container body by means of a joint which allows slipping friction therebetween.

Figure 5:
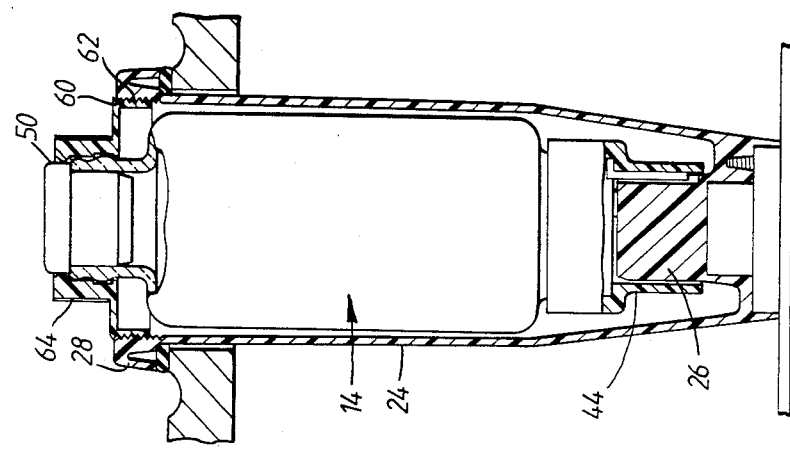
FIGS. 3 to 5 illustrate successive stages of insertion of an alternative embodiment of sample container into the rack.
Figure 4:
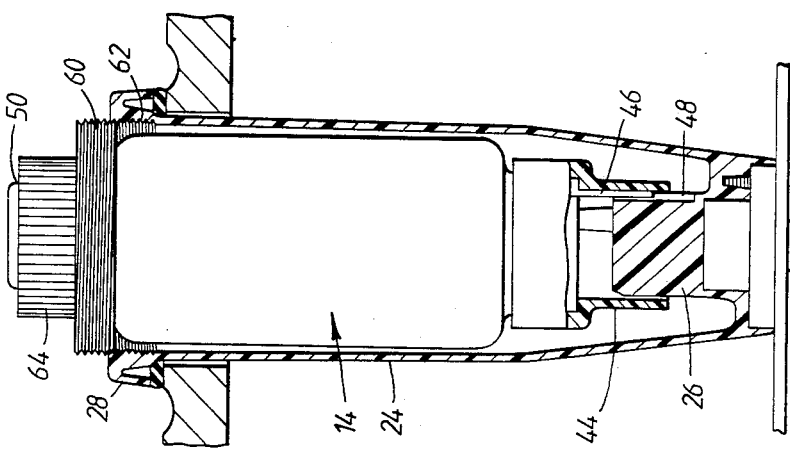
Figure 3:
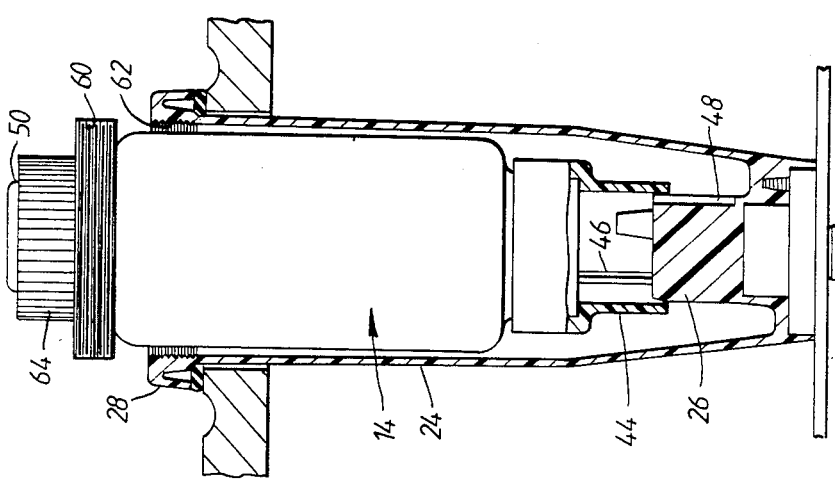

In an alternative embodiment, illustrated in FIGS. 3 to 5, the retention means consist of a screw thread 60 engageable with a threadway 62 on the inner surface of the collar 28 of the containment vessel 24. Instead of the wings 58, the outer surface of the cap is provided with a knurled region 64.

Referring to FIGS. 3 to 5 of the drawings, there are shown three consecutive stages during the insertion of a container 14 into the rack 16. Although these three Figures illustrate the threaded version of the retention means, comparable stages of insertion are carried out for the bayonet means of FIG. 2. A container 14 is first inserted, through the the collar 28 and into the containment vessel 24 which guides the container 14 downwardly until the lower edge region of the socket member 44 rests on the upper edge of the spigot 26. The rib or key 46 does not quite fully extend to the lower free edge of the socket member to enable the initial location between the socket member 44 and the spigot 26 to take place, as is shown in FIG. 3, where the lower end of the rib 46 rests on the upper surface of the spigot 26.

The user now turns the cap 50 and, because of the friction which exists between the cap 50 and the upper neck 35 of the container 14, the container itself rotates about its axis until the rib 46 becomes aligned with the keyway 48. The user can then push the container downwardly, but only so far until the threaded region 60 of the cap 50 rests at the top of the collar 28 i.e. in the position shown in FIG. 4.

The user then operates the retention means by engaging the thread 60 and threadway 62 (or, for the FIG. 2 embodiment, the bayonet joint 54,56) and, because the rib and keyway 46,48 prevent rotation of the socket member 44 on the spigot 26, the container body 34 becomes non-rotational and the cap 50 slips relative to the neck 35 of the container 14 enabling the cap 50 to rotate into threaded or bayonet engagement with the collar 28 of the containment vessel 24.

Once the retention means are fully operational, the container 14 is by then pushed fully home into the position shown in FIG. 5. Tests on a sample previously introduced into the container can commence.

Thus a sample container can be inserted into the rack 16 simply and held there securely and yet be readily released simply by turning the cap 50 to release the threaded connection 60,62 or bayonet joint 54,56, either of which are readily operable by the user from above the upper support plate 20, being disposed adjacent the cap 50 of the container 14.

The base 18 of the rack 16 is formed by a printed circuit board which provides the necessary connections between the electrical contacts 42 at each station and a computer (not shown) which collects, processes and stores the data and which provides a readout of the microbiological growth curve generated by the sample in each of the containers.

As mentioned above, in FIG. 1 it can be seen that a compartment 13 is provided at the back of each drawer 12. The compartment houses an independent power supply and microprocessor 19 to make each drawer as independent as possible of the computer and any power fluctuations. For example a mains supply incorporating a battery may be provided for use in the event of power supply failure so that data logging continues until normal power supply resumes and processor capability is restored. The wall 15 and cover plate 17 of the compartment 13 protect the back-up power supply and microprocessor 19 from any inadvertent spillage in the drawer 12.

Not shown are heating means, such as a coiled heating element disposed at each station, between the upper support plate 20 and the base 18. The heating means enable the sample in a container in the rack to be incubated at a selected temperature of between 30° C. and 40° C. with an accuracy of ±1° C. The drawer microprocessor may be used to control the pattern of heat distribution in the drawer.

There can also be provision for an LED indicator adjacent to each station to show that a container at that station has become "positive", i.e. that a particular concentration of micro-organisms has been reached in that container.

In case any spillage should occur down into the containment vessel, the vessel 24 can be removed from the rack for cleaning or replacement by releasing the bolt 64 which secures it releasably to the base 18. To prevent any potential ingress of spilt sample via the passage provided in the spigot 26 for the electrical contacts 42, there is provided an O ring 66 sealing off this passageway from the base 18.

In use of the apparatus for monitoring blood, a member of the hospital staff takes blood from a patient using a hypodermic syringe and injects the sample immediately from the hypodermic into a container 14 through the upper bung 36. Samples from a number of patients can be collected in this way, the relatively robust containers being then carried to the cabinet 10 and inserted easily and reliably into the rack 16. Tests then commence, with results expected in a matter of hours.

Illustrated in FIG. 1 is a venting plug 70 to which may be inserted through the upper bung 36 of those containers 14 holding samples likely to contain aerobic microbes. Clearly, the cabinet is constructed to give sufficient clearance for the drawers 12 to close when such venting plugs are in use.

Modifications to the illustrated apparatus are also envisaged. For instance, the push-fit plug and socket location means can be interchanged, so that instead of the spigot 26 being disposed on the rack 16 and the socket member 44 on the container 14, the spigot or plug could be provided on the container and vice versa.

Furthermore, the location means could comprise, instead of a push-fit plug and socket means, a screw-thread or bayonet joint means between each container and the rack. Clearly, these alternative embodiments would be suitable where the retention means itself comprises a screw-thread means or bayonet joint means respectively.

An alternative form of orientation means for a location means which comprises a bayonet joint means may suitably comprise the bayonet joint means being radially or circumferentially offset.

We claim:

1. Apparatus for use in detecting micro-organisms in any one of a plurality of samples, comprising a plurality of containers for the samples, each container having a top end and a base, each container having in its base at least one electrode contactable with the sample therein; a container-mounting rack having means for receiving and for locating each of said containers at a respective one of an array of stations, the container-mounting rack having a base and upper support means spaced upwardly from said base, electrical contact means being provided on the base at each said station for electrical connection with the electrode of a container received at the respective station; and releasable retention means adapted to engage the top end of a container and cooperate with the upper support means of the container-mounting rack to retain said container and which are operable from above said upper support means.

2. Apparatus as claimed in claim 1, wherein said retention means comprises means for screw-threaded engagement between each container and the upper support means.

3. Apparatus as claimed in claim 1, wherein said retention means comprises bayonet engagement means between each container and the upper support means.

4. Apparatus as claimed in claim 1, wherein the location means for locating a said container at one of said stations is disposed adjacent the respective electrical contact means at that station.

5. Apparatus as claimed in claim 4, wherein said location means comprises a push-fit plug and socket means.

6. Apparatus as claimed in claim 5, wherein the push-fit plug and socket means is rotationally independent of the retention means.

7. Apparatus as claimed in claim 1, wherein each container has more than one electrode in its base, and a respective number of electrical contacts are provided at each station, the apparatus further comprising orientation means for orienting the container at the respective station so that the electrodes make electrical connection only with their respective electrical contacts.

8. Apparatus as claimed in claim 7, wherein the location means comprises a push-fit plug and socket means and the orientation means comprises a mutually engageable key and keyway on the plug and socket means.

9. Apparatus as claimed in claim 1, wherein the container-mounting rack is provided with heating means for incubating samples in containers which are received in the rack.

10. Apparatus as claimed in claim 1, the container-mounting rack further comprising a containment vessel at each station adapted to surround a container received at that station and to contain spillage therefrom.

11. Apparatus as claimed in claim 10, wherein each said vessel is adapted to be releasably attached to the container-mounting rack.

12. Apparatus as claimed in claim 1, wherein said upper support means of the rack comprises a substantially horizontal plate provided with an indented region at each station for retaining spillage from a container at or adjacent that station.

* * * * *